United States Patent
Schipper et al.

(10) Patent No.: US 11,986,275 B2
(45) Date of Patent: May 21, 2024

(54) OPTICAL VITAL SIGNS SENSOR

(71) Applicant: KONINKLIJKE PHILIPS N.V., Eindhoven (NL)

(72) Inventors: Alphonsus Tarcisius Jozef Maria Schipper, Stramproy (NL); Paulus Henricus Antonius Dillen, Eindhoven (NL); David Antoine Christian Marie Roovers, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1242 days.

(21) Appl. No.: 16/337,218

(22) PCT Filed: Sep. 29, 2017

(86) PCT No.: PCT/EP2017/074918
§ 371 (c)(1),
(2) Date: Mar. 27, 2019

(87) PCT Pub. No.: WO2018/060508
PCT Pub. Date: Apr. 5, 2018

(65) Prior Publication Data
US 2019/0290146 A1   Sep. 26, 2019

(30) Foreign Application Priority Data
Sep. 29, 2016   (EP) .................................. 16191324

(51) Int. Cl.
*A61B 5/024*   (2006.01)
*A61B 5/00*   (2006.01)
*A61B 5/026*   (2006.01)
*A61B 5/0295*   (2006.01)
*A61B 5/1455*   (2006.01)

(52) U.S. Cl.
CPC ........ *A61B 5/02416* (2013.01); *A61B 5/0261* (2013.01); *A61B 5/0295* (2013.01); *A61B 5/14552* (2013.01); *A61B 5/7203* (2013.01); *A61B 5/7207* (2013.01); *A61B 5/7225* (2013.01); *A61B 5/681* (2013.01);
(Continued)

(58) Field of Classification Search
CPC . A61B 5/02416; A61B 5/0261; A61B 5/0295; A61B 5/14552; A61B 5/7203; A61B 5/7207; A61B 5/7225; A61B 5/681; A61B 5/6824; A61B 2560/0204; A61B 2562/0238
See application file for complete search history.

(56) References Cited

U.S. PATENT DOCUMENTS 8,519,322 B2   8/2013   Alameh et al.
2004/0181133 A1   9/2004   Al-Ali
(Continued)

FOREIGN PATENT DOCUMENTS

WO   2015183846 A1   12/2015

*Primary Examiner* — Hien N Nguyen (57) ABSTRACT

An optical vital signs sensor is provided which comprises a PPG sensor (100), a pre-processing unit (130) which adapts the sampling rate or the number of pulses per sample, a processing unit (140) which executes at least one processing algorithm based on an output signal of the pre-processing unit and a sensor control unit (150). The sensor control unit is configured to control the PPG sensor by adapting the sampling rate and/or the number of pulses per sample.

5 Claims, 4 Drawing Sheets

(52) U.S. Cl.
CPC ..... *A61B 5/6824* (2013.01); *A61B 2560/0204* (2013.01); *A61B 2562/0238* (2013.01)

(56) References Cited

U.S. PATENT DOCUMENTS

| | | | |
|---|---|---|---|
| 2011/0077486 A1* | 3/2011 | Watson | A61B 5/0205 |
| | | | 600/324 |
| 2013/0172767 A1 | 7/2013 | Dripps et al. | |
| 2014/0135612 A1 | 5/2014 | Yuen et al. | |
| 2015/0190078 A1 | 7/2015 | Lisogurski | |
| 2016/0029898 A1 | 2/2016 | LeBoeuf et al. | |
| 2017/0249445 A1* | 8/2017 | Devries | A61B 5/742 |
| 2018/0160905 A1* | 6/2018 | Wang | A61B 5/0017 |
| 2018/0279952 A1* | 10/2018 | Orron | A61B 5/318 |

* cited by examiner

OPTICAL VITAL SIGNS SENSOR

This application is the U.S. National Phase application under 35 U.S.C. § 371 of International Application No. PCT/EP2017/074918, filed on 29 Sep. 2017, which claims the benefit of European Application Serial No. 16191324.9, filed 29 Sep. 2016. These applications are hereby incorporated by reference herein.

FIELD OF THE INVENTION

The invention relates to an optical vital signs sensor for monitoring vital signs of a user.

BACKGROUND OF THE INVENTION

Heart rate sensors like optical heart rate sensors are well known to monitor or detect vital signs like a heart rate of a user. Such a heart rate sensor can be based on a photoplethysmograph (PPG) sensor and can be used to acquire a volumetric organ measurement. By means of pulse oximeters, changes in light absorption of a human skin are detected and based on these measurements a heart rate or other vital signs of a user can be determined. The PPG sensors comprise a light source like a light emitting diode (LED) which is emitting light into the skin of a user. The emitted light is scattered in the skin and is at least partially absorbed by the blood. Part of the light exits the skin and can be captured by a photo detector. The amount of light that is captured by the photo detector can be an indication of the blood volume inside the skin of a user. A PPG sensor can thus monitor the perfusion of blood in the dermis and subcutaneous tissue of the skin through an absorption measurement at a specific wave length. If the blood volume is changed due to the pulsating heart, the scattered light coming back from the skin of the user is also changing. Therefore, by monitoring the detected light signal by means of the photo detector, a pulse of a user in his skin and thus the heart rate can be determined. Furthermore, compounds of the blood like oxygenated or de-oxygenated hemoglobin as well as oxygen saturation can be determined.

The PPG sensor can be implemented for example in a smart watch and can be placed in direct contact with the skin of the user. If the PPG sensor is, however, not anymore in direct contact with the skin of the user, e.g. if a loss of skin contact has occurred, the output of the photo detector cannot be used to detect vital signs of a user.

Vital signs of a user can be the heart rate, the respiration rate, the core temperature and the blood pressure of the user.

US 2016/029898 discloses an optical vital signs sensor which has a processor which changes the signal frequency/sampling rate with respect to changes in the activity of the user.

US 2013/0172767 discloses an optical vital signs sensor having a PPG sensor, a pre-processing unit, a processing unit and a sensor control unit.

US 2004/0181133 A1 discloses an optical vital signs sensor having a PPG sensor, a pre-processing unit, a processing unit and a sensor control unit.

US 2014/0135612 A1 discloses an optical vital signs sensor having a PPG sensor, a pre-processing unit, a processing unit and a sensor control unit.

SUMMARY OF THE INVENTION

It is an object of the invention to provide an optical vital signs sensor which allows an improved detection or estimation of vital signs of a user.

This object is solved by an optical vital signs sensor configured to measure and determine vital signs of a user. The optical vital signs sensor comprises a PPG sensor having a light source for generating light which is directed towards a skin of a user as well as a photo detector unit configured to detect light. The light is indicative of the reflection of light emitted in or from the skin of a user. The light of the light source has a sampling frequency, an amplitude, a number of pulses per sample and a duty cycle. The optical vital signs sensor comprises a pre-processing unit coupled to the output of the sensor. The pre-processing unit converts an output signal from the PPG sensor having a first sampling frequency and a first number of pulses per sample into an output signal having a second sample frequency and a second number of pulses per sample in order to neutralize or equalize any changes in sample frequency or the number of pulses per sample. The optical vital signs sensor also comprises a processing unit coupled to the pre-processing unit for processing at least one processing algorithm based on an output signal of the pre-processing unit. The optical vital signs sensor also comprises a sensor control unit configured to control an operation of the PPG sensor by adapting a sampling rate or sampling frequency and/or a number of pulses per sample or a duty cycle.

According to a further aspect of the invention, the pre-processing unit comprises a scaler which receives a number of pulses per sample from the sensor control unit and which is configured to multiply the output signal of the PPG sensor by a factor inversely proportional to the number of pulses in a sample. The pre-processing unit also comprises a down sampler which is adapting the sampling rate of the output signal of the PPG sensor to a desired sampling rate which the down sampler receives from the sensor control unit. According to a further aspect of the invention, the sensor control unit is adapted to receive at least one signal to noise ratio requirement from the processing unit and to determine a sampling rate and/or a number of pulses per sample to achieve the required signal to noise ratio.

According to an aspect of the invention, a method of measuring or determining vital signs of a user with an optical vital signs sensor configured to measure or determine vital signs of a user is provided. The optical vital signs sensor is a PPG sensor having a contact surface, at least one light source for generating light which is directed towards a skin of the user and at least one photo detector unit configured to detect light which is indicative of a reflection of light emitted in or from the skin of the user. An output signal of the PPG sensor has a sampling rate, an amplitude, a number of pulses per sample and a duty cycle. Light from the at least one light source is emitted towards the skin of the user and the reflected light is detected by a photo detector. An output signal from the PPG sensor having a first sampling frequency and a first number of pulses is converted into an output signal having a second sampling frequency and a second number of pulses per sample in order to neutralize or equalize any changes in sample frequency or number of pulses.

According to an aspect of the invention, a computer program product comprising a computer readable memory storing computer program code means for causing the optical vital signs to carry out the steps of measuring or determining vital signs of a user as described above is provided.

According to an aspect of the invention, the vital signs sensor comprises a LED based PPG sensor. The LED light penetrates the skin of the user, is reflected and some of it can reach a photo detector. The output of the photo detector can be used to monitor a blood volume fraction and blood compounds like oxygenated and de-oxygenated hemoglobin. In particular, the amount of absorption or reflectance of the light from the LED light source can be used to determine the heart rate as well as the blood volume fraction or blood compounds. The heart rate relates to the blood volume fraction. Furthermore, the PPG sensor according to the invention is therefore an optical sensor allowing a non-invasive measurement of vital signs of a user.

It shall be understood that a preferred embodiment of the present invention can also be a combination of the dependent claims or above embodiments or aspects with respective independent claims.

These and other aspects of the invention will be apparent from and elucidated with reference to the embodiment(s) described hereinafter.

DETAILED DESCRIPTION OF EMBODIMENTS

Figure 1:
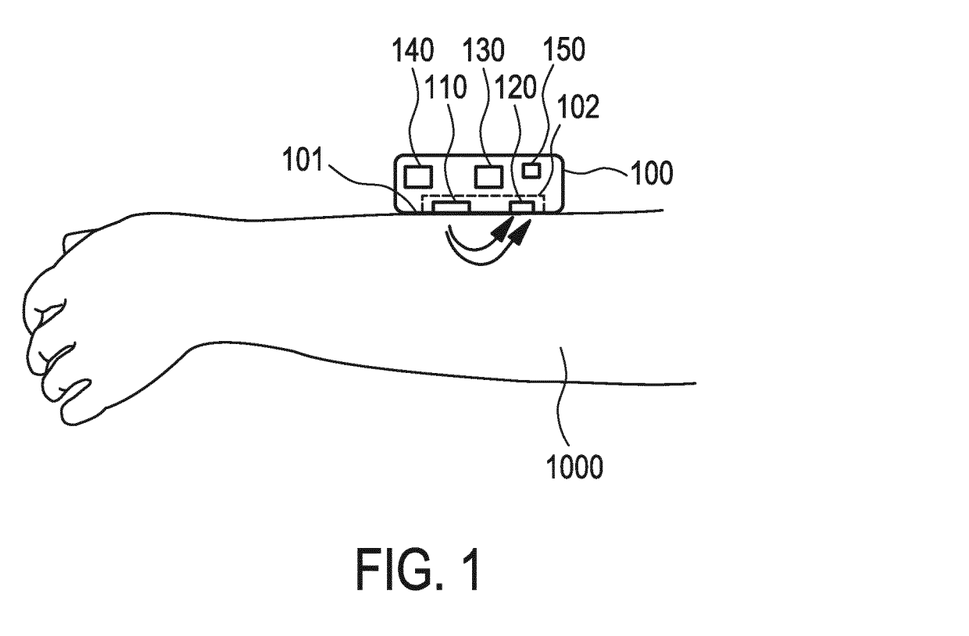
FIG. 1 shows a schematic representation of an optical vital signs sensor according to the invention.

FIG. 1 shows a basic representation of an operational principle of an optical vital signs sensor. In FIG. 1, the optical vital signs sensor, e.g. a heart rate sensor 100, with its contact surface 101 is arranged or placed on for example an arm of a user. The contact surface 101 can be (directly) placed onto the skin 1000 of the user. The heart rate sensor 100 comprises a PPG sensor 102 which comprises at least one light source 110 and at least one photo detector 120. The light source 110 emits light via the contact surface 101 onto or in the skin 1000 of a user. Some of the light is reflected and the reflected light can be detected by the photo detector 120. Some light can be transmitted through tissue of the user and be detected by the photo detector 120. Based on the reflected light, vital signs of a user like a heart rate can be determined.

Figure 2:
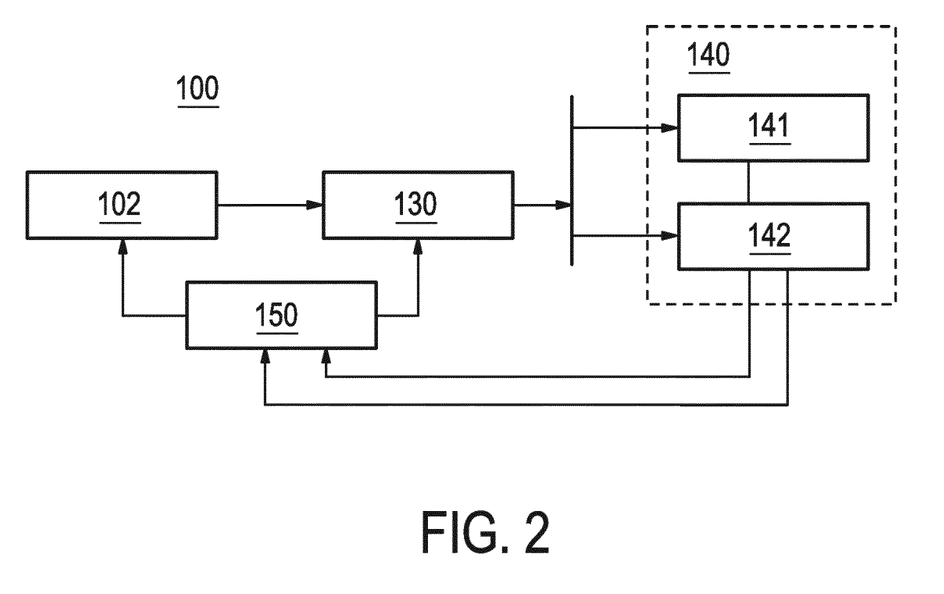
FIG. 2 shows a schematic block diagram of an optical vital signs sensor according to an aspect of the invention.

FIG. 2 shows a schematic block diagram of an optical vital signs sensor according to an aspect of the invention. The optical vital signs sensor 100 comprises a PPG sensor 102, a pre-processing unit 130, a processing unit 140 and a sensor control unit 150. The PPG sensor 102 generates a signal that has a signal to noise ratio, an output power, an amplifier gain, a sampling frequency and a number of light pulses constituting a sample (alternatively a duty cycle of the light). The operation of the PPG sensor 102 is controlled by the sensor control unit 150. In other words, the sensor control unit 150 sets the light power, the amplifier gain, the sampling frequency and/or the duty cycle of the light of the PPG sensor 102. The pre-processing unit 130 serves to neutralize or equalize any changes in the sampling frequency or the number of light pulses per sample. The pre-processing unit 130 is coupled to the processing unit 140, which can process the received data. In particular, several processing algorithms can be executed by the processing unit 140. The pre-processing unit 130 serves to convert an output signal from the sensor 102 having a first sample frequency and a first number of pulses per sample into an output signal having a second sample frequency and a second number of pulses per sample. In particular, the pre-processing unit 130 can output one value per sample regardless of the numbers of LED pulses and may serve to remove any changes in the sample frequency and/or the number of light pulses such that the processing unit is decoupled from any such changes. Thus, the processing unit 140 will not notice any changes in the sample frequency, the duty cycle and the number of pulses in the output signal of the sensor 102.

The sensor control unit 150 receives from the processing unit 140 the signal to noise ratios as required by the processing algorithms processed in the processing unit 140. The sensor control unit 150 will adapt the sample frequency and the number of pulses per sample of the sensor accordingly. The sensor control unit 150 also controls the adaptation of the sample frequency, sample rate, number of pulses and/or duty cycle accordingly and forwards this to the pre-processing unit 130. The pre-processing unit 130 thus acts as a converter for the processing unit 140 such that any changes in the sampling frequency, the number of pulses, the duty cycle etc. at the output of the sensor 102 will not disturb the processing of the processing unit. The processing unit 140 sends a requested signal to noise ratio to the sensor control unit 150. The sensor control unit 150 configures the sensor such that the requested signal to noise ratio is met. This can be performed by adjusting four parameters, namely the LED sampling frequency, the LED number of pulses per sample, the LED amplitude and/or the receiver gain. If another request was made by one of the algorithm processings, then the sensor control unit can choose to meet the required signal to noise ratio by adapting the LED sampling frequency and/or the number of LED pulses to ensure that the output signals of the pre-processing unit 130 to the processing unit 140 is not disrupted.

According to an aspect of the invention, the sensor control unit can control the LED sampling frequency, the LED number of pulses per sample (i.e. the duty cycle), the LED amplitude (or LED power) as well as the receiver gain. It should be noted that an adaptation of the LED amplitude and the receiver gain can lead to disruptions of the signal. According to the aspect of the invention, however, the LED sampling frequency as well as the number of pulses can be adapted without disrupting the output signal of the processing units. To achieve this, the control unit combines the request from the different processing units. If a first request arrives, then the control uses all freedom to set up the sensor by using all four parameters. In this case, no disruption of the signal is present as none of the other processing algorithms are using the signal. However, if a second request arrives, then it must be chosen that the sensor control unit only selects and adapts the sampling frequency and the number of pulses in order to avoid any disruption in the signal.

According to the invention, a sample of the sensor may consist of a number of pulses. The sample value of the sample corresponds to the sum of the values of the individual pulses. The samples have a sampling rate.

Figure 3:
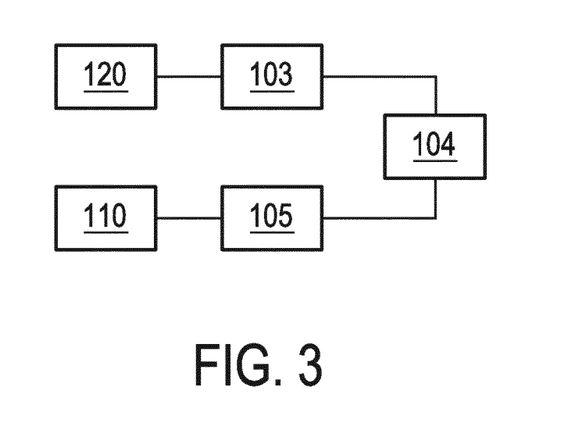
FIG. 3 shows a schematic block diagram of the PPG sensor of FIG. 2.

FIG. 3 shows a schematic block diagram of the PPG sensor of FIG. 2. The PPG sensor 102 comprises a light source 110, a photo detector 120, an amplifier 103, an analogue/digital converter 104 and a control unit 105. The light source 101 can comprise several LEDs. For example, the light source may comprise two green LEDs and one infrared IR LED. The photo detector may comprise at least one photo diode. The output of the photo detector 120 is amplified by the amplifier 103. The output of the amplifier 103 can be directly or indirectly be coupled to the analogue/digital converter 104 which converts the output of the amplifier. The control unit 105 serves to control the operation of the light source 110. In particular, the control unit 105 can adapt the output power, the gain, the number of pulses, the sampling frequency and/or the duty cycle of the LEDs in the light source. Thus, the sensor 102 can be controlled by the control unit 105 according to the required configuration. Through the control unit 105, the operation of the sensor can be adjusted to meet the requirements of the processing unit. It should be noted that the output power, the number of pulses per sample, the amplifier gain and the sampling rate or sampling frequency influences the overall signal to noise ratio of the sensor.

Figure 4:
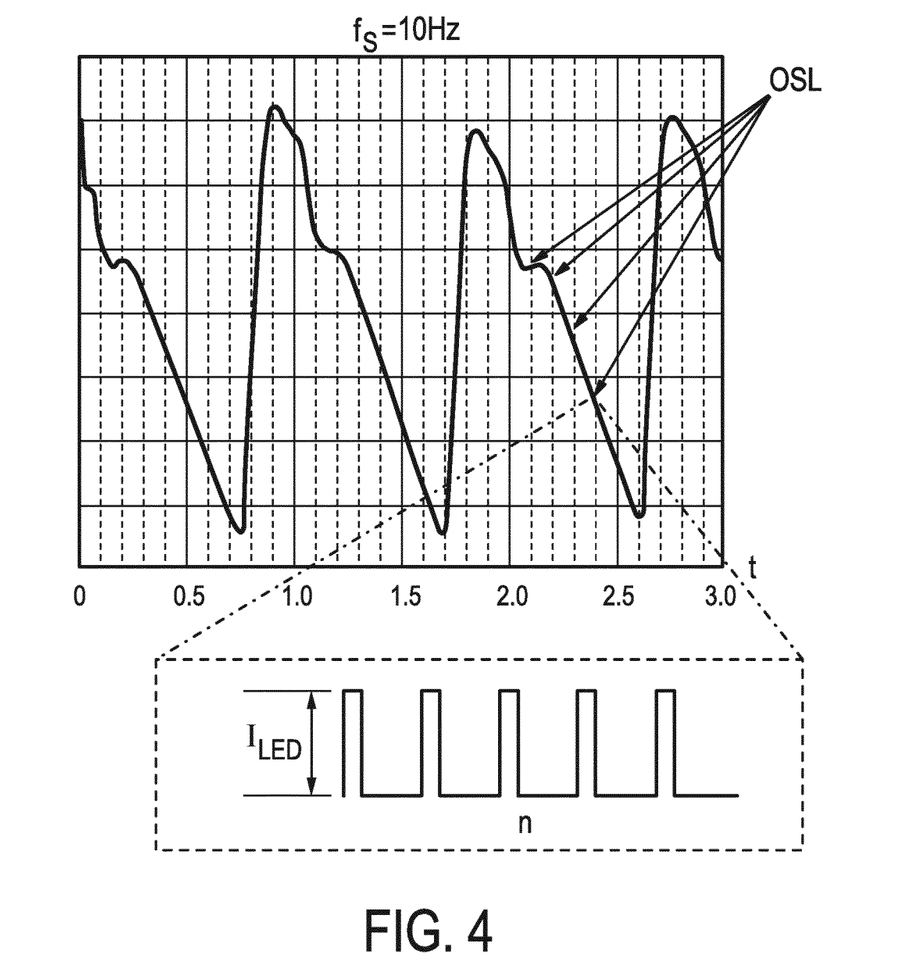
FIG. 4 shows a graph indicating the output signal of the PPG sensor 102.

FIG. 4 shows a graph indicating the output signal of the sensor 102. In FIG. 3, the sampling frequency is 64 Hz. As shown in FIG. 3, each sample of the output signal of the photo detector is based on a number of pulses of the light source. Thus, one sample corresponds to n pulses from the light source. The amplitude of the pulses corresponds to the current $I_{led}$ of the LEDs. In FIG. 4, several optical sampling locations OSL are depicted. Accordingly, one sample corresponds to n pulses. The sample value then corresponds to the sum of the values of the individual pulses. The sample has a sample frequency of $f_{SAMPLE}$. The sample frequency can range from 32 to 1042 Hz. The pulses constituting one sample may be emitted in a burst. The pulse direction is for example 3 μs.

Figure 5:
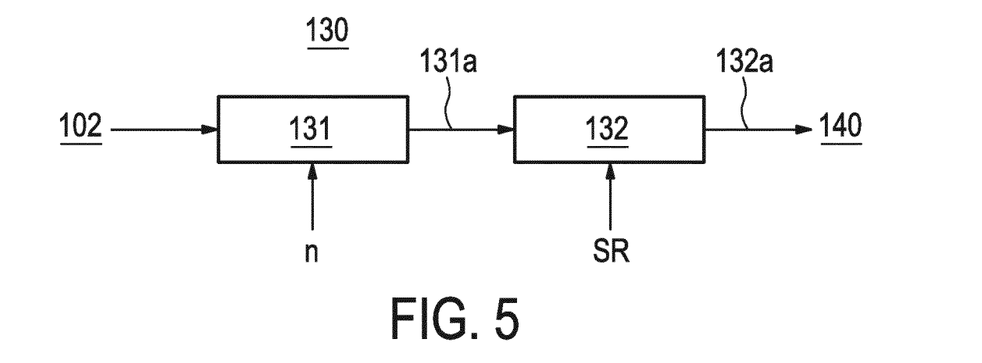
FIG. 5 shows a block diagram of the pre-processing unit 130.

FIG. 5 shows a block diagram of the pre-processing unit 130. The pre-processing unit 130 comprises a scaler 131 and a down sampler 132. The scaler 131 receives the output from the sensor 102 and the number n of pulses of the light from the light source. The down scaler 132 receives the output 131a of the scaler 131 and the sampling rate SR of the sensor 102. The output 132a of the down sampler 132 is forwarded to the processing unit 140.

In the scaler 131, the output signal of the sensor 102 is multiplied by a factor inversely proportional to the number n of pulses in a sample. The down sampler 132 adapts the sampling rate to a desired sampling rate SR, for example 32 Hz. This can be performed by a serious of down samplers which each reduces the sampling rate by a factor of 2. Accordingly, the sampling rate of the sensor 102 is preferably 32 Hz multiplied by the power of 2. Thus, the sampling rate can be 32 Hz, 64 Hz, 128 Hz etc.

According to an aspect of the invention, the scaler 131 and the down sampler 132 can be operated on the fly avoiding a disruption of the signal. In other words, the scaler and the down sampler can react to changes or desired changes in the sampling rate.

Figure 6:
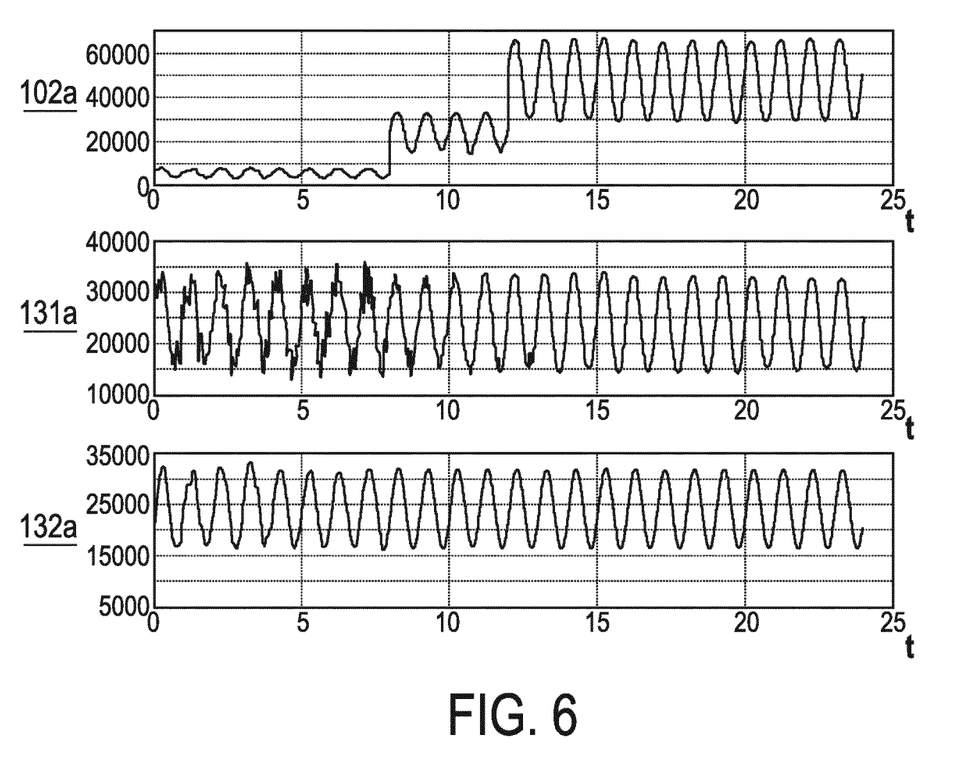
FIG. 6 shows a graph indicating a time sense of an output signal of the sensor.

FIG. 6 shows a graph indicating a time sense of an output signal of the sensor. In FIG. 6, the output signal 102a of the sensor 102 is depicted. In the intervals from t=0 to t=8 s, the number of LED pulses is 1. In the interval from t=8 to t=12 s, the number of LED pulses is 2. In the interval from t=12 to t=24 s, the number of LED pulses is 8. As can be seen from FIG. 6, the amplitude of the output signal increases with the number of pulses. In the middle of FIG. 6, the output signal 131a of the scaler 131 is depicted. As can be seen, only the sampling rate varies across the depicted area. In fact, the sampling rate increases from left to right.

In FIG. 6, also the output signal 132a of the down sampler 132 is depicted. This signal 132a is the input signal of the processing unit 140. As can be seen, only the signal to noise ratio, but not the sampling rate varies. Thus, this signal is not disruptive.

According to an aspect of the invention, the processing unit 140 may be able to process at least two processing algorithms 141, 142. The first processing algorithm 141 may be different from the second processing algorithm 142. Typically, each processing unit 141, 142 has a requirement for the signal to noise ratio. These requirements are output to the sensor control unit 150 which will adapt the sampling rate of the sensor 102 accordingly.

The output signal 132a of the pre-processing unit 130 has a fixed scale and a fixed sampling rate. According to an aspect of the invention, the first processing algorithm 141 may be used to determine the heart rate and thus in particular processes the pulsatile part of the signal. The first processing algorithm 141 may measure the amplitude of the pulsatile signal, i.e. the AC component of the signal. It should be noted that the amplitude of this AC component of the output signal can vary over time such that depending on the amplitude, the requested or required signal to noise ratio may increase or decrease.

A second processing algorithm 142 may perform a different processing. Such a processing could for example be an inter beat interval processing algorithm that may not require a signal in case of severe motion. In such a case, the signal to noise ratio may be set to zero.

According to a further aspect of the invention, the processing algorithm may be used to determine the average heart rate. Such a processing algorithm may increase the required signal to noise ratio under certain motion conditions.

According to the invention, if a processing algorithm is deactivated, the processing unit may set the requested signal to noise ratio to zero indicating that no signal is required.

The sensor control unit 150 receives the required signal to noise ratios from the processing unit. The sensor control unit 150 thus adapts the number of pulses and/or the sampling rate of the sensor 102. Preferably, this can be done dynamically.

According to the invention, the sensor control unit 151 may comprise a lookup table. Table 1 discloses an example of such a lookup table.

| Signal to noise ratio (dB) | Number of pulses | Sampling rate (Hz) | Power (mW) |
| --- | --- | --- | --- |
| 55 | 1 | 32 | 0.096 |
| 58 | 1 | 64 | 0.192 |
| 61 | 1 | 128 | 0.384 |
| 64 | 1 | 256 | 0.768 |
| 67 | 1 | 512 | 1.536 |
| 70 | 1 | 1024 | 3.072 |
| 73 | 2 | 1024 | 6.144 |
| 76 | 4 | 1024 | 12.288 |

This lookup table comprises a relation between a desired signal to noise ratio and the number of pulses as well as a sampling rate. In this example, for a certain LED power and receiver gain, the dependency of the signal to noise ratio is depicted wherein two of the four parameters are variable while the other two parameters are fixed.

As an example, if the required signal to noise ratio is 60 dB, then the sensor control unit 150 may select the third row which corresponds to a signal to noise ratio of 61 wherein the number of pulses is 1 and the sampling rate is 128. The resulting power is 0.384 mW.

According to an aspect of the invention, the sensor control unit 150 may also be able to implement a dynamic non-uniform sampling. In any words, the sampling scheme of the sensor 102 can be dynamically changed from uniform to non-uniform sampling. In a non-uniform sampling, the sampling rate of the sensor 102 may vary over time. A higher sampling rate will locally increase the signal to noise ratio. As an example, such a higher sampling rate may be selected for intervals where a heart beat is expected. In the other intervals between heart beats, the sampling rate may be reduced.

The vital signs sensor 100 can be implemented as a PPG sensor or may comprise a PPG sensor. The output signal of the PPG sensor gives an indication on the blood movement in vessels of a user. The quality of the output signal of the PPG sensor can depend on the blood flow rate, skin morphology and skin temperature. In addition, optical losses in the PPG sensor may also have an influence on the quality of the output signal of the PPG sensor. The optical efficiency of the PPG sensor can depend on reflection losses when light penetrates from one media into another. Furthermore, scattering of light at the surface of the skin of the user may also have an influence on the optical efficiency of the PPG sensor. The PPG sensor or optical vital signs sensor according to an aspect of the invention can be implemented as a device that requires a contact with the skin of the user such as a wrist worn device (like a watch or smart watch).

Other variations of the disclosed embodiment can be understood and effected by those skilled in the art in practicing the claimed invention from a study of the drawings, the disclosure and the appended claims.

In the claims, the word "comprising" does not exclude other elements or steps and in the indefinite article "a" or "an" does not exclude a plurality.

A single unit or device may fulfil the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. An optical vital signs sensor configured to measure or determine vital signs of a user, the optical vital signs sensor comprising:
 a photoplethysmographic (PPG) sensor having a light source configured to generate light which is directed towards a skin of the user and a photo detector unit configured to detect light,
  wherein said light being indicative of a reflection of light emitted in or from the skin of the user, and
  wherein an output signal of the PPG sensor has a sampling rate, an amplitude, a number of pulses per sample and a duty-cycle;
 a pre-processing unit coupled to an output of the PPG sensor and being configured to convert an output signal from the PPG sensor having a first sample frequency and a first number of pulses per sample into an output signal having a second sample frequency and a second number of pulses per sample in order to neutralize or equalize any changes in sample frequency or the number of pulses per sample, wherein the pre-processing unit includes:
  a scaler which receives a number of pulses per sample from a sensor control unit and which is configured to multiply the output signal of the PPG sensor by a factor inversely proportional to the number n of pulses in a sample; and
  a down sampler which adapts the sampling rate of the output signal of the PPG sensor to a desired sampling rate (SR) which the down sampler receives from the sensor control unit;
 a processing unit coupled to the pre-processing unit and being configured to execute at least one processing algorithm for generating a control output based on an output signal of the pre-processing unit; and
 the sensor control unit coupled to the processing unit and configured to control an operation of the PPG sensor by adapting the sampling rate (SR) and/or the number (n) of pulses per sample based on the control output of the processing unit.

2. The optical vital signs sensor according to claim 1,
 wherein the output of the processing unit is at least one signal to noise ratio requirement; and
 wherein the sensor control unit is further configured to determine the sampling rate and/or the number of pulses per sample to achieve the required signal to noise ratio.

3. The optical vital signs sensor according to claim 1, wherein the sensor control unit is further configured to control the operation of the PPG sensor by adapting an output power of the light source and/or a receiver gain of the PPG sensor.

4. A method of measuring or determining vital signs of a user with an optical vital signs sensor configured to measure or determine vital signs of a user,
 said optical vital signs sensor being a PPG sensor having a contact surface, at least one light source for generating light which is directed towards a skin of a user and at least one photo detector unit configured to detect light which is indicative of a reflection of light emitted in or from the skin of a user,
 wherein an output signal of the PPG sensor has a sampling rate, an amplitude, a number of pulses per sample and a duty cycle,
 the method comprising the steps of:
 emitting, by the optical vital signs sensor, light from at least one light source towards the skin of the user and detecting the reflective light by the at least one photo detector;
 converting, by the optical vital signs sensor, an output signal from the PPG sensor having a first sample frequency and a first number of pulses per sample into an output signal having a second sample frequency and a second number of pulses per sample in order to neutralize or equalize any changes in sample frequency or the number of pulses,
  wherein the converting of the output signal from the PPG sensor includes receiving a number of pulses per sample from a sensor control unit and which is configured to multiply the output signal of the PPG sensor by a factor inversely proportional to the number n of pulses in a sample, and adapting the sampling rate of the output signal of the PPG sensor to a desired sampling rate (SR) which a down sampler receives from the sensor control unit;

processing, by the optical vital signs sensor, at least one processing algorithm for generating a control output based on the converting of the output signal from the PPG sensor; and controlling, by the optical vital signs sensor, an operation of the PPG sensor by adapting the sampling rate and/or the number of pulses per sample based on the control output.

5. A non-transitory computer program product comprising a computer readable memory storing computer program code means for causing the optical vital signs sensor according to claim 1 to carry out the steps of measuring or determining vital signs of a user.

\* \* \* \* \*